(12) United States Patent
Kurnik et al.

(10) Patent No.: US 6,309,351 B1
(45) Date of Patent: *Oct. 30, 2001

(54) METHODS FOR MONITORING A PHYSIOLOGICAL ANALYTE

(75) Inventors: Ronald T. Kurnik, Foster City; Janet Tamada, Belmont; Michael Tierney, San Jose; Russell Owen Potts, San Francisco, all of CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/650,024

(22) Filed: Aug. 28, 2000

Related U.S. Application Data

(63) Continuation of application No. 08/933,025, filed on Sep. 18, 1997, which is a continuation of application No. 08/580,212, filed on Dec. 28, 1995, now abandoned.

(51) Int. Cl.$^7$ ........................................................ A61B 5/00
(52) U.S. Cl. ........................... 600/309; 600/345; 600/365; 600/573
(58) Field of Search .................................. 600/309, 345, 600/348, 363, 366, 573, 584; 128/898–899

(56) References Cited

U.S. PATENT DOCUMENTS

| | | |
|---|---|---|
| 4,457,748 | 7/1984 | Lattin et al. . |
| 4,953,552 | 9/1990 | DeKarzo . |
| 4,981,779 | 1/1991 | Wagner . |
| 4,986,271 | 1/1991 | Wilkins . |
| 5,001,051 | 3/1991 | Wagner . |
| 5,036,861 | 8/1991 | Sembrowich et al. . |
| 5,050,604 | 9/1991 | Reshef et al. . |
| 5,076,273 | 12/1991 | Schoendorfer et al. . |
| 5,086,229 | 2/1992 | Rosenthal et al. . |
| 5,139,023 | 8/1992 | Stanley et al. . |
| 5,140,985 | 8/1992 | Schroeder . |
| 5,165,407 | 11/1992 | Wilson et al. . |
| 5,250,419 | 10/1993 | Bernard et al. . |
| 5,279,543 | 1/1994 | Gilkfeld et al. . |
| 5,291,887 | 3/1994 | Stanley et al. . |
| 5,362,307 | 11/1994 | Guy et al. . |
| 5,364,838 | 11/1994 | Rubsamen . |
| 5,458,140 | 10/1995 | Eppstein et al. . |
| 5,460,177 | 10/1995 | Purdy et al. . |
| 5,582,184 | 12/1996 | Eppstein et al. . |
| 5,722,397 | 3/1998 | Eppstein . |
| 5,746,217 | 5/1998 | Erickson et al. . |
| 5,820,570 | 10/1998 | Erickson et al. . |
| 5,823,973 | 10/1998 | Racchini et al. . |
| 5,885,211 | 3/1999 | Eppstein et al. . |

FOREIGN PATENT DOCUMENTS

| | | |
|---|---|---|
| 0 154 684 | 9/1985 | (EP) . |
| 0 304 304 A2 | 2/1989 | (EP) . |
| 0 513 789 A2 | 11/1992 | (EP) . |
| 0 649 628 A1 | 4/1993 | (EP) . |
| 62-133937 | 6/1987 | (JP) . |
| WO 96/00110 | 1/1996 | (WO) . |
| WO 98/28037 | 7/1998 | (WO) . |

OTHER PUBLICATIONS

U. S. Patent Application #08/933,025, of Kurnik et al., filed Sept. 18, 1997, class 600/subclass 309.*
Sahya et al., "Percutaneous Electrophoresis of Amino Acids and Urea," *Medical & biological Engineering & Computing* 16 : 126–134 (1978).
Glikfeld, Peretz et al., "Noninvasive Sampling of Biological Fluids by Iontophorosis, " Pharmaceutical Research 6 :988–990 (1989).
Kurnik et al., "Application of the Mixtures of Experts Algorithm for Signal Processing in a Noninvasive Glucoso Monitoring System," *Sensors and Actuators B 60* :19–26 (1999).
Kurnik et al., "Design and Simulation of a Reverse Iontophorectic Glucoso Monitoring Device, " *J. Electro Soc.* 145 (12):4120–4125 (1998).
Meyeroff et al., "On Line Continuos Monitoring of Subcutaneous Tissue Glucoso in Men by Combining Protable Glucosensor With Microdialysis, " *Diabetologia* 35 :1087–1092 (1992).
Rao et al., "Iontphoretic and Noninvasive Glucose Monitoring, " School of Pharmacy, University of California San Francisco Proceed. Intern. Symp. Control. Rel. Bioact. Mater...Controlled Released Society, Inc. *21* :1–2 (1994).
Santi, Patricia, et al., "Reverse Iontophoresis–Parameters Determining Electrosmotic Flow; I. oH and Ionic Strength," *Journal of Controlled Release 38* : 159–165 (1996).
Tamada, Janet et al., "Measurement of Glucose in Diabetic Subjects Using Noninvasive Transdermal Extraction, " Nature Medicine 1:1198–1201 (1995).
Tamada et al., "Noninvasive Glucose Monitoring, " *JAMA 282* (19): 1839–1844 (1999).

* cited by examiner

*Primary Examiner*—John P. Lacyk
*Assistant Examiner*—Ryan Carter
(74) *Attorney, Agent, or Firm*—Barbara McClung; Robins & Pasternak LLP

(57) ABSTRACT

A method for continual monitoring of a physiologic analyte in a subject includes steps of contacting the subject with a collection reservoir such that the analyte can move from the subject into the collection reservoir, the contents of the collection reservoir being in operative communication with a detector, collecting the analyte in the collection reservoir, using the detector to detect the analyte in the collection reservoir, and, once the analyte has been detected, rendering the analyte undetectable by the detector. Also, apparatus for continual monitoring of a physiologic analyte in a subject includes a collection reservoir for receiving the analyte from the subject, the contents of the collection reservoir being in operative relationship with a detector that detects the analyte in the reservoir, and means for rendering the analyte, once detected, undetectable by the reservoir.

39 Claims, No Drawings

METHODS FOR MONITORING A PHYSIOLOGICAL ANALYTE

This application is a continuation of U.S. patent application Ser. No. 08/933,025, filed Sep. 18, 1997, now pending, which is a continuation of U.S. patent application Ser. No. 08/580,212, filed Dec. 28, 1995, now abandoned, from which application(s) priority is claimed pursuant to 35 U.S.C. §120 and which application(s) are incorporated herein by reference in its(their) entirety(entireties).

FIELD OF THE INVENTION

This invention relates to continual measurement of indicia of the physiological state of a subject, and particularly to continual measurement of analytes in tissues and body fluids of a subject.

BACKGROUND OF THE INVENTION

The physiologic state of a subject can by monitored by measurement of certain indicia.

Some such indicia, including the familiar "vital signs" such as the subject's body temperature, heart rate, respiratory rate, and the like can be measured directly either without resort to instrumentation, or by use of simple instruments placed onto a body surface or within a body cavity. Body temperature measurement, for example, can be made directly by use of a thermometer or thermistor placed on the skin or within a body cavity. Other indicia of physiologic state that can be measured directly require the use of more complex instrumentation. Such indicia include electrocardiography and electroencephalography, for example, and the instrumentation for measuring such indicia may include apparatus affixed to the subject's skin or implanted within the body.

Biochemical indicia of a subject's physiologic state can provide highly useful information. Such biochemical indicia include the presence and amounts in the subject's tissue or body fluids of certain chemical species; by way of example, such chemical species may be or may have been ingested by or administered to the subject, or they may be metabolic products or byproducts or metabolic precursors, or they may constitute parts of the subject's metabolic apparatus, such as enzymes and hormones and the like. Thus, the presence or amount of a drug or drug metabolite, for example in a sample of a subject's blood or urine, can provide an indication of the subject's history of use of the drug, or can provide an assurance that a dosage or route of administration is providing a suitable therapeutic level in the subject's tissues. And, as a well-known example, a measure of the amount of glucose in a subject's blood, or of ketones in the subject's urine, can provide useful information for management of hypoglycemia and hyperglycemia, particularly in diabetics.

Such biochemical indicia can be measured, for example, in a sample of a fluid or tissue removed from the subject's body; blood work and urinalysis, routine or more complete, for example, can provide information regarding such indicia. Where the subject's physiologic state may change significantly over short periods of time, samples for analysis of biochemical indicia may be taken more frequently.

For some physiologic conditions the time scale for changes in the physiologic state can be short, so that removal and analysis of the appropriate sample at a preferred frequency is impractical. It is generally understood, for example, that more frequent sampling and analysis of a diabetic person's blood glucose, together with careful management of the person's sugar and insulin, can provide an improvement in quality of life and the lifespan of the diabetic; but removal of the blood sample is painful, and the apparatus surrounding the analysis of the sample is cumbersome and inconvenient to use.

For some types of biochemical indicia, then, there is a need for methods for "continual" monitoring, that is to say, for measuring the biochemical indicia over extended monitoring time periods (for example, around the clock; or 24 hours per day throughout the week; etc.) substantially without interruption, or in a continuing series of measurements at appropriately spaced intervals.

In some instances detectors may be available to directly detect the biochemical indicia in the range of concentrations that are pertinent to monitoring the physiologic state of the subject. In these instances, the detector may be implanted and left to reside within the tissue or internal body space, where the detector measures the biochemical analyte as it comes within detectable range of the detector, and records or transmits the resulting data for further use.

In other instances the biochemical indicia may not be directly detectable by known detectors. In these instances some treatment of the analyte is required as a step preliminary to detection. Such treatment may, for example, result in the analyte (or the analyte together with some other substance involved in the treatment) having a particular spectrum of radiation absorption (detectable for example colorimetrically) or of radiation (detectable for example by fluorescence detection). Or, the treatment may entail a specific chemical reaction (as for example by a substrate-specific catalyst such as an enzyme) that results in generation of a chemical species (for example an ion) that is directly detectable using a known detector.

Where some treatment of the analyte is required, a reservoir may be employed for collecting the analyte and carrying out the treatment. Such a reservoir can be held in operational proximity to (in some instances in contact with) the detector and within or in contact with a tissue or surface of the body of the subject to be monitored. Conveniently, the reservoir can for example be placed on the subject's skin; in this instance the analyte passes into the reservoir through the skin surface (the movement can be facilitated by a potential gradient), where it undergoes the treatment and is then detected.

Irrespective of the technique of detections where the analyte is continually collected, it can accumulate in the reservoir, resulting in a progressively higher measurement over time, resulting in decreased reliability in subsequent measurements over the monitoring period.

SUMMARY OF THE INVENTION

In one general aspect the invention features a method for continual monitoring of a physiologic analyte in a subject, by contacting the subject with a collection reservoir such that the analyte can move from the subject into the collection reservoir, the collection reservoir being in contact with a detector, collecting the analyte in the collection reservoir, using the detector to detect the analyte in the collection reservoir, and, once detection of the analyte is accomplaished, rendering the analyte undetectable by the detector.

In some embodiments the analyte itself is not directly detected by the detector, but is instead processed through a detection cascade, the final step of which occurs at the detector. In such embodiments the step of using the detector to detect the analyte includes steps of treating the analyte to generate a detectable signal or a detectable chemical species that is detected by the detector. In some embodiments the step of treating the analyte includes contacting the analyte with a catalyst, such as an enzyme, that reacts with the analyte to produce a detectable chemical species; in preferred such embodiments the reaction of the catalyst and the enzyme further results in conversion of the analyte to a reaction product that is not detected by the detector (that is, the reaction product is removed from the detection cascade); and in preferred such embodiments the detection of the detectable chemical species by the detector results in conversion of the detectable chemical species to a reaction product that is not detected by the detector.

As a result, whether the analyte is detected directly by the detector, or is instead detected indirectly by being treated in a cascade of reactions resulting in a detectable signal or detectable chemical species which is detected by the detector, the potential for detection of each analyte molecule is extinguished once detection occurs. As a significant consequence, there is no accumulation, over the monitoring time period, of detectable signal or of detectable chemical species or of the analyte itself once detection has occurred. For any measurement at any time during the monitoring time, only that detectable analyte or detectable signal which has entered the collection reservoir since the previous measurement, or that detectable signal or detectable chemical species that has been produced since the previous measurement, is measured. The detector itself can therefore operate over a narrower dynamic range than would be required if detectable analyte or signal or detectable chemical species were permitted to accumulate over time. Significantly, there is no need for a differential measurement; that is, there is no accumulated measure to subtract from the instant measurement, and thus potential compounding of error, notoriously problematic where differential measurements are required, is avoided. Moreover, saturation or the collection/detection system with the analyte is avoided by conversion of the analyte.

In some embodiments the collection reservoir is contacted with a surface of the subject's skin, and the analyte moves from the subject through the skin surface into the collection reservoir, in most instances under the influence of a potential gradient such as an osmotic or ionic gradient, or an electrical or magnetic gradient, or a hydrostatic pressure gradient, for example; in some such embodiments the analyte moves passively through the skin surface, or its movement is enhanced by application of electrical energy (for example, by electroosmosis or by electrophoresis) or ultrasound energy (by sonophoresis), or the permeability of the skin to its movement is enhanced by applying to the skin surface a sweat inducing substance (such as, for example, pilocarpine) or a skin permeation enhancer.

In another general aspect the invention features apparatus for continual monitoring of a physiologic analyte in a subject, the apparatus including a collection reservoir for receiving the analyte from the subject, the contents of the collection reservoir being in operative communication with a detector that detects the analyte in the reservoir, and means for rendering the analyte undetectable by the reservoir.

In some embodiments the analyte itself is not directly detected by the detector, and the reservoir contains analyte interacting means, which upon contact with the analyte results in production of a detectable signal or a detectable chemical species that is detected by the detector. In some such embodiments the analyte and the analyte contacting means associate to create a binding couple, and the detectable signal is generated by the association. In other such embodiments the analyte contacting means is a catalyst, such as an enzyme, which upon contact with the analyte produces the detectable signal or detectable chemical species; in preferred such embodiments the catalyst or enzyme reacts with the analyte itself, and the result is conversion of the analyte to a reaction product that is undetectable by the detector as well as production of the detectable signal or detectable chemical species. Because each molecule of the analyte can effectively react only once with the catalyst, the undetectable reaction product passes out of the detection cascade.

In a particularly preferred embodiment, for continual measurement of blood glucose, the analyte is glucose, and the analyte contacting means is an enzyme (for example, a glucose oxidase) that acts upon the glucose to substantially irreversibly produce a detectable chemical species (for example, hydrogen peroxide) and an undetectable reaction product (for example, gluconic acid); and the detect or is an electrode that senses the detectable chemical species by a substantially irreversible electrochemical redox reaction (for example, conversion of hydrogen peroxide to water and liberating oxygen).

DESCRIPTION OF PREFERRED EMBODIMENTS

Before the method and apparatus of the invention is described and disclosed it is to be understood that this invention is not limited to the particular components or compositions described as such may, of course, vary. It is also to be understood that the terminology used herein is for the purpose of describing particular embodiments only, and is not intended to be limited, as the scope of the invention will be limited only by the appended claims.

It must be noted that as used in this specification and the appended claims, the singular forms "a", "an" and "the" include plural referents unless the context clearly dictates otherwise. Thus, for example, reference to "a molecule" includes a plurality of molecules and different types of molecules.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited in connection with.

In a preferred embodiment of the invention, for continual monitoring of glucose, the collection reservoir is applicable to the subject's skin, it contains an electrolyte and a glucose oxidase, which in a coupled reaction in the presence of oxygen converts glucose to gluconic acid, generating hydrogen peroxide. The detector is an electrode that detects hydrogen peroxide in a redox reaction. Such a collection and detection scheme, and apparatus for carrying it out, is disclosed for example in copending patent applications U.S. Ser. Nos. 08/373,931; 08/501,664; 08/526,732, pertinent parts of which are hereby incorporated herein by reference. Here, the analyte (glucose), which is not directly detected by the detector, passes from the subject transdermally into the collection reservoir, where it contacts the enzyme (glucose oxidase), which reacts with the analyte to produce a detectable chemical species (hydrogen peroxide) and in the same reaction converts the analyte to a reaction product (gluconic acid) that is not detected by the detector; when activated, the detector (electrode sensor) detects the detectable chemical species and, in the same (redox) reaction, converts it to an undetectable chemical species. As a result, each molecule of glucose that enters the reservoir and is processed through the detection cascade is detected only once.

In this example, as in others, the detector needn't be activated throughout the collection period; copending patent applications U.S. Ser. Nos. 08/265,844, 08/265,048, 08/373, 931 disclose, among other matters, various schemes in which collection cycles alternate with detection cycles throughout the monitoring time. In these particular examples, suppressing (or not activating) detection during collection provides for a short time interval in which the analyte (glucose) enters the collection reservoir and is there converted by reaction with a catalyst (glucose oxidase) to a nondetectable chemical species (gluconic acid) and to a detectable chemical species (hydrogen peroxide); during this short collection interval the detectable species (hydrogen peroxide) accumulates. Then the detector is activated, and the accumulated detectable species (hydrogen peroxide) is simulataneously detected and converted (by the redox reaction) into a nondetectable chemical species. An advantage of this scheme can be that it provides for availablity of a higher quantity of hydrogen peroxide to the sensing electrode during the measurement cycle, so that the electrode need not be as sensitive as would be required if the electrode remained activated throughout the collection cycle, and measuring hydrogen as it evolved from the detection cascade. While this can be an advantage in some circumstances, it is not necessarily a requirement, as the sensitivity of the electrode can be increased, or the detectable signal may be elevated by other techniques.

Further in the examples described in U.S. Ser. Nos. 08/265,844, 08/265,048, 08/373,931, the method further includes a step of applying an electrical (iontophoretic) current to the skin, to assist by electroosmosis the transdermal movement of the glucose into the collection reservoir. A further motivation for suppressing (or not activating) the detector during the collection phase is avoidance of possible conflict between the iontophoretic current and the detection current produced at the sensor. Such considerations would not pertain where an electric current is not applied; and any such conflicts can be avoided by other techniques.

Thus, whether detection is suppressed (or not activated) during collection, providing for a short accumulation period before measurement, or not, it can be advantageous according to the present invention to render the analyte (and any detectable signals or species) undetectable, once detection of the analyte has been accomplished either directly or indirectly.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. A method for monitoring a physiologic analyte in a subject, comprising steps of:
    (a) collecting the analyte in a collection reservoir, wherein
        (i) said collection reservoir is in contact with the subject such that the analyte can move from the subject into said collection reservoir, and (ii) the collection reservoir is in operative contact with a detector;
    (b) contacting the analyte in the collection reservoir with an enzyme that reacts with the analyte to produce a detectable chemical species, wherein the reaction of the analyte and the enzyme further results in conversion of the analyte to a reaction product that is not detected by the detector;
    (c) using the detector to detect the detectable chemical species in the collection reservoir, and once the detectable chemical species has been detected, rendering the detectable chemical species undetectable by the detector; and
    (d) repeating steps (a), (b) and (c).

2. The method of claim 1, wherein the analyte is glucose.

3. The method of claim 2, wherein the enzyme is an enzyme that acts upon the glucose to produce a detectable chemical species and an undetectable reaction product.

4. The method of claim 3, wherein the enzyme is glucose oxidase.

5. The method of claim 4, wherein said detectable chemical species is hydrogen peroxide and said undetectable reaction product is gluconic acid.

6. The method of claim 1, wherein the collection reservoir comprises the enzyme.

7. The method of claim 1, wherein the collection reservoir comprises an electrolyte.

8. The method of claim 7, wherein the collection reservoir further comprises glucose oxidase.

9. The method of claim 1, wherein the analyte is glucose and the collection reservoir comprises an electrolyte and glucose oxidase.

10. A method for monitoring a physiologic analyte in a subject, comprising steps of:
    (a) collecting the analyte in a collection reservoir by applying energy to a skin surface of the subject, wherein (i) said collection reservoir is in contact with the skin surface of the subject such that the analyte can move from the subject into said collection reservoir, and (ii) the collection reservoir is in operative contact with a detector;
    (b) contacting the analyte in the collection reservoir with an enzyme that reacts with the analyte to produce a detectable chemical species, wherein the reaction of the analyte and the enzyme further results in conversion of the analyte to a reaction product that is not detected by the detector;
    (c) using the detector to detect the detectable chemical species in the collection reservoir, and once the detectable chemical species has been detected, rendering the detectable chemical species undetectable by the detector; and
    (d) repeating steps (a), (b) and (c).

11. The method of claim 10, wherein the analyte is glucose.

12. The method of claim 11, wherein the enzyme is an enzyme that acts upon the glucose to produce a detectable chemical species and an undetectable reaction product.

13. The method of claim 12, wherein the enzyme is glucose oxidase.

14. The method of claim 13, wherein said detectable chemical species is hydrogen peroxide and said undetectable reaction product is gluconic acid.

15. The method of claim 10, wherein the collection reservoir comprises the enzyme.

16. The method of claim 10, wherein the collection reservoir comprises an electrolyte.

17. The method of claim 16, wherein the collection reservoir further comprises glucose oxidase.

18. The method of claim 10, wherein the analyte is glucose and the collection reservoir comprises an electrolyte and glucose oxidase.

19. The method of claim 10, wherein the energy applied is electrical energy.

20. The method of claim 19, wherein the electrical energy is iontophoretic current.

21. The method of claim 19, wherein (i) the analyte is glucose, (ii) the collection reservoir comprises an electrolyte and glucose oxidase, and (iii) the electrical energy is iontophoretic current.

22. The method of claim 10, wherein the energy applied is ultrasound energy.

23. The method of claim 10, further comprising the step of applying to the skin surface a sweat inducing substance.

24. The method of claim 10, further comprising the step of applying to the skin surface a skin permeation enhancer.

25. A method for monitoring a physiologic analyte in a subject, wherein the method comprises the steps of:
  (a) collecting the analyte in a collection reservoir by applying energy to a skin surface of the subject, wherein (i) said collection reservoir is in contact with the skin surface of the subject such that the analyte can move from the subject into said collection reservoir, and (ii) the collection reservoir is in operative contact with a detector;
  (b) discontinuing collection of the analyte by discontinuing the application of energy, while the collection reservoir remains in contact with the skin surface of the subject;
  (c) contacting the analyte in the collection reservoir with an enzyme that reacts with the analyte to produce a detectable chemical species, wherein (i) the reaction of the analyte and the enzyme further results in conversion of the analyte to a reaction product that is not detected by the detector, and (ii) said contacting of the analyte is carried out while the collection reservoir remains in contact with the skin surface of the subject;
  (d) detecting the detectable chemical species in the collection reservoir using the detector, and once the detectable chemical species has been detected, rendering the detectable chemical species undetectable by the detector, said detecting performed while the collection reservoir remains in contact with the skin surface of the subject;
  (e) discontinuing detection after substantially all the detectable chemical species has been detected and rendered undetectable, thereby preventing significant accumulation of detectable chemical species in the collection reservoir; and
  sequentially repeating steps (a), (b), (c), (d), and (e) while the collection reservoir remains in contact with the skin surface of the subject.

26. The method of claim 25, wherein the analyte is glucose.

27. The method of claim 26, wherein the enzyme is an enzyme that acts upon the glucose to produce a detectable chemical species and an undetectable reaction product.

28. The method of claim 27, wherein the enzyme is glucose oxidase.

29. The method of claim 28, wherein said detectable chemical species is hydrogen peroxide and said undetectable reaction product is gluconic acid.

30. The method of claim 25, wherein the collection reservoir comprises the enzyme.

31. The method of claim 25, wherein the collection reservoir comprises an electrolyte.

32. The method of claim 31, wherein the collection reservoir further comprises glucose oxidase.

33. The method of claim 25, wherein the analyte is glucose and the collection reservoir comprises an electrolyte and glucose oxidase.

34. The method of claim 25, wherein the energy applied is electrical energy.

35. The method of claim 34, wherein the electrical energy is iontophoretic current.

36. The method of claim 34, wherein (i) the analyte is glucose, (ii) the collection reservoir comprises an electrolyte and glucose oxidase, and (iii) the electrical energy is iontophoretic current.

37. The method of claim 25, wherein the energy applied is ultrasound energy.

38. The method of claim 25, further comprising the step of applying to the skin surface a sweat inducing substance.

39. The method of claim 25, further comprising the step of applying to the skin surface a skin permeation enhancer.

* * * * *